(12) United States Patent
Kelly et al.

(10) Patent No.: US 10,328,237 B2
(45) Date of Patent: Jun. 25, 2019

(54) READY TO USE CATHETER ASSEMBLY AND METHOD OF MAKING A READY TO USE CATHETER ASSEMBLY

(71) Applicant: Teleflex Life Sciences Unlimited Company, Hamilton (BM)

(72) Inventors: Ronald John Kelly, Oranmore (IE); Alan Fitzgerald, Edgesworthtown (IE); Morgan Tierney, Tullamore (IE); Volkmar Schulz, Herrenberg (DE); Bernhard Hiesch, Schoemberg (DE)

(73) Assignee: Teleflex Life Sciences Unlimited Company, Hamilton (BM)

( * ) Notice: Subject to any disclaimer, the term of this patent is extended or adjusted under 35 U.S.C. 154(b) by 0 days.

(21) Appl. No.: 15/465,108

(22) Filed: Mar. 21, 2017

(65) Prior Publication Data

US 2017/0274176 A1   Sep. 28, 2017

(30) Foreign Application Priority Data

Mar. 24, 2016   (EP) .................................... 16000709

(51) Int. Cl.
*A61M 25/00*   (2006.01)
*A61M 25/01*   (2006.01)
(Continued)

(52) U.S. Cl.
CPC ...... *A61M 25/002* (2013.01); *A61M 25/0017* (2013.01); *A61M 25/01* (2013.01);
(Continued)

(58) Field of Classification Search
CPC .............. A61M 25/0017; A61M 25/01; A61M 25/0111; A61M 25/002; A61M 25/001;
(Continued)

(56) References Cited

U.S. PATENT DOCUMENTS

| 2,947,415 A | * | 8/1960 | Garth | ...................... A61L 2/206 |
| | | | | 206/364 |
| 3,967,728 A | * | 7/1976 | Gordon | ............... A61M 25/002 |
| | | | | 206/364 |

(Continued)

FOREIGN PATENT DOCUMENTS

| EP | 2 703 035 A1 | 3/2014 |
| WO | 2007/050685 A2 | 5/2007 |

(Continued)

*Primary Examiner* — Chun Hoi Cheung
(74) *Attorney, Agent, or Firm* — Baker & Hostetler LLP

(57) ABSTRACT

A ready to use catheter assembly comprises a catheter package with an opening, a catheter with a shaft arranged in the catheter package so a distal end of the catheter lies in the region of the opening, and a protective sleeve which partly covers the catheter shaft, a first end of the protective sleeve fixed to the distal end of the catheter. A method for producing a ready to use catheter assembly and a ready to use catheter assembly which further reduces the risk of an accidental contamination of a catheter when pulling it out of the catheter package prior to the insertion into the urethra of a user are provided. The opening has a defined maximum opening length, a second end of the protective sleeve is releasably connected which the catheter package near the maximum opening length of the opening and the protective sleeve is in a retracted state.

16 Claims, 1 Drawing Sheet

(51) Int. Cl.
  *A61M 27/00*      (2006.01)
  *B65B 55/08*      (2006.01)
  *B65B 55/16*      (2006.01)
  *B65B 61/20*      (2006.01)
  *B65D 75/32*      (2006.01)
  *B65D 75/58*      (2006.01)
  *B65D 81/22*      (2006.01)
  *B65D 85/24*      (2006.01)

(52) U.S. Cl.
  CPC .......... *A61M 25/0111* (2013.01); *A61M 27/00* (2013.01); *B65B 55/08* (2013.01); *B65B 55/16* (2013.01); *B65B 61/20* (2013.01); *B65D 75/325* (2013.01); *B65D 75/58* (2013.01); *B65D 81/22* (2013.01); *B65D 85/24* (2013.01)

(58) Field of Classification Search
  CPC ... A61M 25/011; A61M 27/00; B65D 75/325; B65D 75/38; B65D 81/22; B65D 85/24; B65D 75/58; B65B 55/08; B65B 55/16; B65B 61/20
  USPC .................. 206/210, 571, 364, 438, 205
  See application file for complete search history.

(56) References Cited

U.S. PATENT DOCUMENTS

| | | | | |
|---|---|---|---|---|
| 6,613,014 B1* | 9/2003 | Chi | .............. | A61M 25/0097 604/93.01 |
| 7,476,223 B2* | 1/2009 | McBride | ............. | A61M 25/002 206/210 |
| 7,615,045 B2* | 11/2009 | Israelsson | ................ | A61F 5/44 604/544 |
| 7,770,726 B2* | 8/2010 | Murray | ............... | A61M 25/002 206/210 |
| 7,823,722 B2* | 11/2010 | Bezou | ................. | A61M 25/002 206/210 |
| 7,918,831 B2* | 4/2011 | House | .................. | A61M 25/00 604/192 |
| 8,459,455 B2* | 6/2013 | Frojd | ....................... | B65B 5/04 206/364 |
| 9,033,149 B2* | 5/2015 | Terry | ................ | A61M 25/0017 206/364 |
| 9,707,375 B2* | 7/2017 | Conway | ............ | A61M 25/0017 |
| 2005/0049577 A1* | 3/2005 | Snell | ................ | A61M 25/0009 604/544 |
| 2005/0109648 A1* | 5/2005 | Kerzman | ............ | A61M 25/002 206/364 |
| 2006/0163097 A1* | 7/2006 | Murray | ............. | A61M 25/0009 206/364 |
| 2008/0091145 A1* | 4/2008 | House | ................. | A61M 25/002 604/171 |
| 2008/0172042 A1* | 7/2008 | House | ............... | A61M 25/002 604/544 |
| 2011/0056852 A1* | 3/2011 | Frojd | ....................... | B65B 5/04 206/210 |
| 2011/0114520 A1* | 5/2011 | Matthison-Hansen | | A61M 25/002 206/364 |
| 2015/0273180 A1* | 10/2015 | Schonfeldt | ....... | A61M 25/0017 206/210 |
| 2015/0352321 A1* | 12/2015 | Hannon | ........... | A61M 25/0067 604/544 |
| 2016/0220784 A1* | 8/2016 | Palmer | ............. | A61M 25/0017 |
| 2016/0339205 A1* | 11/2016 | Foley | ................. | A61M 25/002 |

FOREIGN PATENT DOCUMENTS

WO      2010/006620 A1      1/2010
WO      2014/074141 A1      5/2014

* cited by examiner

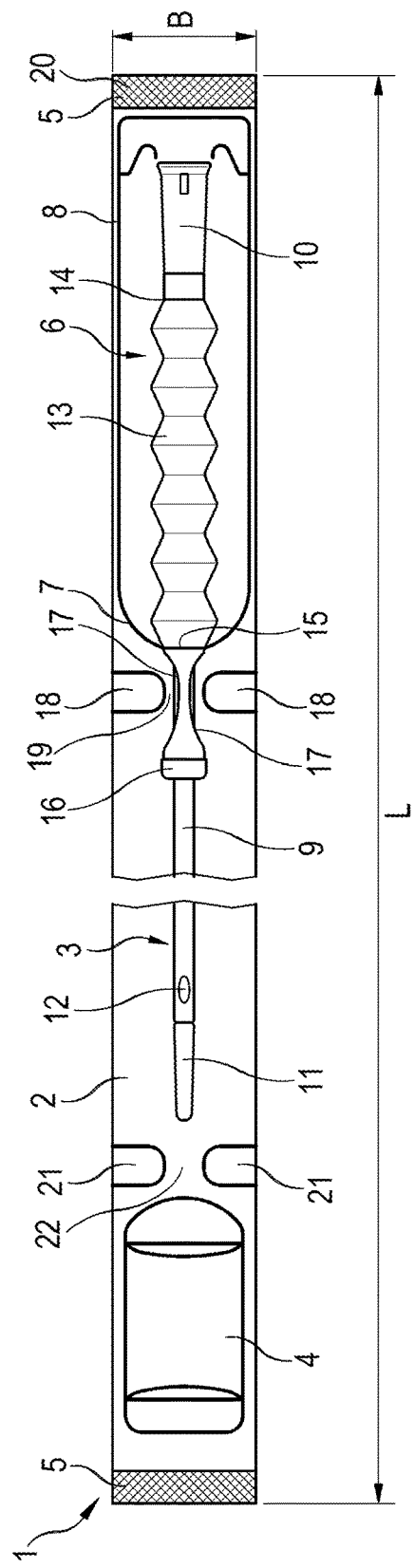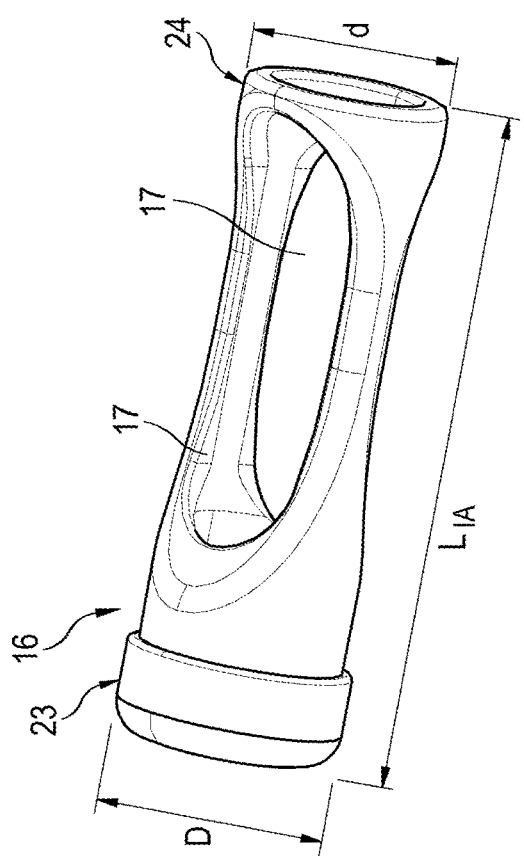
Fig. 1
Fig. 2

READY TO USE CATHETER ASSEMBLY AND METHOD OF MAKING A READY TO USE CATHETER ASSEMBLY

CROSS-REFERENCE TO RELATED APPLICATIONS

This application claims priority to foreign European patent application No. EP 16000709.2, filed on Mar. 24, 2016, the disclosure of which is incorporated by reference in its entirety.

FIELD OF THE INVENTION

The present patent application refers to a ready to use catheter assembly comprising a catheter package with an opening means, a catheter with a catheter shaft which is arranged in the catheter package so that a distal end of the catheter lies in the region of the opening means, and a protective sleeve which at least partly covers the catheter shaft, a first end of the protective sleeve is fixed to a distal end of the catheter.

Furthermore, the patent application also refers to a method of making such a ready to use catheter assembly.

BACKGROUND

Ready to use catheter assemblies are often used for intermittent catheterization by users without control of the bladder. This is often the case after spinal cord injuries. Therefore, these catheter assemblies must be easy to use and must allow a safe application even for users with limited manual dexterity. As the catheter of the ready to use catheter assembly is used for intermittent catheterization, it must have a low-friction surface to avoid injuries of the urethra wall when inserting the catheter into the urethra. As these catheters are very slippery when touched, the handling of the catheters is even more difficult.

In order to avoid infections of the urinary tract, the whole catheterization process must be as sterile as possible. Therefore, direct hand contact with at least the parts of the catheter that are inserted into the urethra should be avoided.

WO 2010/006620 A1 already shows a catheter assembly used for intermittent catheterization. The catheter assembly comprises a hydrophilic coated catheter with a protective sleeve that at least partly surrounds the catheter shaft. In a storage position, the protective sleeve is compressed at a distal end of the catheter. The distal end of the protective sleeve is attached to the connector of the catheter and the proximal end of the protective sleeve is attached to the package by a weak attachment. When the catheter package is opened, and the catheter is removed from the package, the protective sleeve is pulled over the catheter shaft until its maximum length is reached. Thereafter, the weak attachment between the sleeve and the package breaks and the catheter with the protective sleeve can be completely removed from the package. However, when opening the package, uncovered parts of the catheter shaft are exposed to the exterior and can be accidentally touched by the user or objects in the surroundings of the catheter and can be contaminated so that they are no longer in a sterile state.

SUMMARY OF THE INVENTION

Therefore, it is the object of the present patent application to provide a ready to use catheter assembly which overcomes the disadvantages of the devices known from the prior art and which especially reduces the risk of an inadvertent contamination of the catheter when opening the catheter package.

These objects are achieved by a ready to use catheter assembly with an opening means which has a defined maximum opening length and wherein a second end of the protective sleeve is releasably connected with the catheter package near the maximum opening length of the opening means and the protective sleeve is in a retracted state.

The term "distal end" refers to the end of the catheter facing away from the body of the user when the catheter is brought in the use position shortly before the insertion of the catheter shaft into the urethra. Therefore, the distal end of the catheter is the end of the catheter where the funnel is attached.

The term "proximal end" refers to the other end of the catheter, namely, the end of the catheter with the catheter tip.

With the term "near the maximum opening length" it is meant that there is less than a finger's breadth between the connection of the protective sleeve to the catheter package and the maximum opening length of the opening means.

With the catheter assembly according to the present invention, the whole part of the catheter shaft that is exposed to the exterior when opening the catheter package via the opening means is covered by the retracted protective sleeve. Therefore, no accidental contact between the catheter shaft and the user, which is usually the fingers of the user, or other objects in the surroundings of the catheter, is possible. The catheter then stays in the sterile state until the insertion into the urethra. As at least a part of the catheter shaft is exposed in the package, because the protective sleeve is retracted, an easy wetting of the catheter in the package is possible.

Preferably, the length of the protective sleeve in an extended state is at least ⅔ of the length of the catheter shaft. In this way, the part of the catheter shaft which is covered by the protective sleeve after removing it from the catheter package and before the insertion into the urethra is long enough to ensure that no accidental contamination of the catheter shaft can occur. Nevertheless, easy handling of the catheter during insertion into the urethra is possible.

The ready to use catheter assembly may further comprise an introducer aid in the form of a hollow cylinder arranged on the catheter shaft, the introducer aid is fixedly connected with the second end of the protective sleeve and releasably connected with the catheter package near the maximum opening length of the opening means. As catheters for intermittent catheterization are usually very slippery to facilitate insertion in the urethra, they are difficult to handle, especially for users with reduced dexterity. The introducer aid allows an easy and safe handling and introduction of the catheter in the urethra and a secure connection between the package and the protective sleeve which can nevertheless be easily released.

Advantageously, the catheter package comprises at least one protrusion which is in releasable engagement with the introducer aid. The protrusion of the catheter package and the introducer aid with the protective sleeve fixed thereto are then form locked. When the catheter is pulled out of the catheter package, the protective sleeve is extended until its total length is reached. Then, the pulling force must be augmented somewhat so that the form lock connection between the protrusion of the catheter package and the introducer aid is released and the catheter can be completely pulled out of the catheter package.

Preferably, the at least one protrusion of the catheter package is a weld tab. Such a weld tab can be easily produced when the complete catheter package is closed via weld seams.

Furthermore, the releasable connection between the catheter package and the introducer aid with the protective sleeve attached thereto can be improved when the introducer aid comprises at least one recess which is in releasable engagement with the at least one protrusion of the catheter package.

The at least one recess of the introducer aid may have a stopper at the end facing the distal end of the catheter and an inclination at the end facing the proximal end of the catheter. The stopper prevents the introducer aid from moving in the direction of the catheter tip. The inclination helps to pull the introducer aid through the passage formed by the protrusion or weld tab when pulling the catheter out of the catheter package.

Preferably, the at least one recess of the introducer aid completely penetrates the wall of the introducer aid. Therefore, when gripping the introducer aid, the user automatically grips the catheter shaft through the recess and has very good control of the catheter during the complete catheterization process.

The protective sleeve may be made of a flexible material. Preferably, the protective sleeve is made from ethylene-vinyl acetate (EVA). However, the protective sleeve could also be made of stiffer materials, for example polyethylene. As long as the wall thickness is sufficiently thin, the desired flexibility is achieved. Due to the flexible material, the protective sleeve can be easily retracted and extended which also leads to an easy insertion process of the catheter.

The protective sleeve may be fixed to the introducer aid along the complete length of the introducer aid. Therefore, the protective sleeve also covers the at least one recess in the introducer aid and thus covers the catheter shaft which extends through the introducer aid. The catheter shaft is protected against contaminations and the user has good control of the slippery catheter shaft.

The length of the catheter shaft that is covered by the protective sleeve in the retracted state may correspond to at least ¼ of the complete length of the catheter shaft. This guarantees that a user can easily grip the catheter through the protective sleeve when pulling the catheter out of the catheter package. Preferably, the maximum length of the catheter shaft that is covered by the protective sleeve in the retracted state is ½ of the complete length of the catheter shaft. In this case, it can still be guaranteed that the complete catheter shaft is activated and wetted.

The diameter of the proximal end of the introducer aid may correspond to at least 0.75 times the theoretical diameter of a passage in the catheter package created by the at least one protrusion of the catheter package. This allows the pulling of the catheter out of the catheter package without exerting an excessive force on the catheter and the catheter package. The passage in the catheter package is formed by the two layers of foil held together by the protrusion/weld tab in the package. The length of the foil material of the two layers can be transformed in a theoretical diameter. The theoretical diameter is two times the length of the passage divided by $\pi$.

The catheter assembly may further comprise a sachet for wetting fluid which is arranged in the catheter package near the catheter tip so that it is not in not in contact with the catheter. This arrangement facilitates the wetting and activation of the catheter.

Preferably, the catheter package comprises a first compartment for the sachet for the wetting fluid and a second compartment for the catheter and the two compartments are in permanent fluid communication with each other. Due to the fluid communication, the wetting fluid is guided along a defined passage in the catheter package and is directed to the catheter shaft for wetting and activation thereof. Preferably, two weld seams are provided in the catheter package which form the two compartments. A passage between the weld seams enables the fluid communication between the two compartments. The catheter tip faces this passage so that the wetting fluid is directed towards the catheter tip and flows down along the catheter shaft.

The catheter shaft may be at least partly covered with an activated hydrophilic coating. The catheter assembly therefore comprises a pre-activated catheter which is ready for use. The activation of the catheter shaft takes place during the manufacturing process so that a safe activation of the complete coating can be guaranteed. The user does not need to perform any steps before using the catheter but only needs to open the package, remove the catheter and can directly start with the intermittent catheterization.

It is a further object of the present patent application to provide a solution for making a ready to use catheter assembly as described above which leads to a preactivated catheter which can be stored without suffering quality losses, which allows a secure and easy activation of the catheter, and which leads to a catheter assembly with an improved contamination protection.

This object is solved by a method for making a ready to use catheter assembly as described above which comprises the following steps: Placing the hydrophilic coated catheter with the introducer aid and the protective sleeve in the catheter package so that the protective sleeve is in a retracted position in the region of the opening means with the defined opening length, placing the wetting fluid into the catheter package so that it is not in contact with the catheter, sterilizing the complete catheter assembly, and then activating the hydrophilic coating of the catheter by bringing the wetting fluid into contact with the hydrophilic coating. As the protective sleeve is in the retracted state, the catheter shaft can be easily brought into contact with the wetting fluid during the activation step. As the sterilization takes place before the activation of the hydrophilic coating of the catheter, degradation of the hydrophilic coating during sterilization and storage of the catheter package is avoided.

BRIEF DESCRIPTION OF THE DRAWINGS

In the following the invention is described in more detail with the aid of drawings:

FIG. 1 shows a ready to use catheter assembly in a partly broken view and

FIG. 2 shows a perspective view of an introducer aid of the ready to use catheter assembly as shown in FIG. 1

DETAILED DESCRIPTION

FIG. 1 shows the ready to use catheter assembly 1. The ready to use catheter assembly comprises a catheter package 2 that is made of a material which is impermeable to water vapour, for example an aluminum foil composite or multi-layer material, LDPE, MDPE, HDPE, LLDPE, PP, PET or siloxane coatings.

A catheter 3 and a sachet 4 for wetting fluid are arranged inside the catheter package 2. The catheter package 2 has an elongated form so that its length L is substantially longer than its width B. The catheter package 2 is closed at both its longitudinal ends with an end weld seam 5. The catheter package 2 is further provided with an opening means 6. The opening means 6 is formed by a package opening 7 cut through the material of the catheter package 2 and closed by a sealing flap 8 in such a manner that the catheter package 2 remains impermeable to water and water vapor and the contents of the catheter package remain in a sterile state.

The catheter 3 comprises a catheter shaft 9 which is provided at one end, the distal end, with a funnel 10 and at the other end, the proximal end, with a catheter tip 11. Near the catheter tip 11, the catheter shaft 9 is provided with at least one catheter eye 12 through which urine can enter into the catheter shaft 9 and flow through the catheter shaft 9 to the funnel 10 where it exits the catheter when the catheter is inserted in the urethra of a user. The catheter shaft 9 is at least partly covered by a protective sleeve 13. One end of the protective sleeve 13, the first or distal end 14, is fixedly connected to the funnel 10. The other end of the protective sleeve 13, the second or proximal end 15, is releasably attached to the catheter package 2. This is achieved by an introducer aid 16 arranged on the catheter shaft 9. The proximal end 15 of the protective sleeve 13 is fixed to the introducer aid 16, for example by an adhesive bond and/or heat shrinking. The introducer aid 16 is releasably connected to the catheter package 2.

The introducer aid 16 has the form of a hollow cylinder and is slidably arranged on the catheter shaft 9 so that it can slide on the catheter shaft 9 in both directions without any friction and without causing any damage to the outer surface of the catheter shaft 9. Therefore, the inner channel of the introducer aid 16 is slightly larger than the outer diameter of the catheter shaft 9. The introducer aid 16 has a length $L_{IA}$ of approximately 35 mm. The introducer aid 16 comprises two recesses 17 on opposite sides thereof. The recesses 17 are elongated and penetrate the complete wall of the introducer aid 16 so that they form openings or apertures in the wall of the introducer aid 16. If the catheter is used in a clean environment, for example by a user wearing sterile gloves, the recesses do not need to be covered. In the embodiment shown in the figures, the recesses 17 are covered by the protective sleeve 13. The protective sleeve can be inserted in the inner channel of the introducer aid. Another possibility is to slip the protective sleeve of the outer surface of the introducer aid 16. The protective sleeve 13 is attached to the introducer aid 16 along nearly the complete length $L_{IA}$ thereof, so that at least the recesses 17 are completely covered by the protective sleeve 13. When inserting the catheter 3, the user grips the catheter shaft 9 through the recesses 17. The protective sleeve 13 ensures the sterile state and facilitates handling of the slippery catheter shaft 9.

The catheter 3 is arranged in the catheter package 2 so that its distal end with the funnel 10 is arranged in the region of the package opening 7. The catheter package 2 is provided with two weld tabs 18 which form a passage 19 inside the catheter package 2. The introducer aid 16 is arranged in the catheter package 2 so that the two weld tabs 18 of the catheter package 2 are in engagement with the two recesses 17 of the introducer aid 16. The passage 19 has a theoretical diameter which corresponds to twice the length of the passage divided by π. The diameter D of the introducer aid 16 at the proximal end thereof is at least ¾ of the theoretical diameter of the passage 19. After the production of the catheter package 2, the catheter package 2 relaxes and the passage 19 adopts an oval form and tightens around the smallest part of the introducer aid 16, the recesses 17. Due to the structural constraints of the catheter package 2 caused by the geometry of the weld tabs and the stiffness of the package material, the desired interference fit of the introducer aid 16 in the catheter package 2 is achieved. In this way, the introducer aid 16 and therewith the complete catheter 3 are fixed in the catheter package 2.

The distance between the weld tabs 18 and a first end 20 of the catheter package 2 is at least 100 mm. As the protective sleeve 13 is fixed at one end 14 to the funnel 10 and at the other end 15 to the introducer aid 16, it is in a retracted state and only covers the catheter shaft 9 in the region between the introducer aid 16 and the funnel 10. The package opening 7 is formed by a non-closed loop which is cut in the material of the catheter package 2 and extends approximately from the first end 20 of the catheter package 2 to the weld tabs 18 of the catheter package 2. The length of the package opening 7 defines a maximum opening length in the catheter package 2. There are small distances between the opening 7 and the weld tabs 18 as well as the end 20 of the catheter package 2. The length of the catheter shaft 9 covered by the introducer aid and the protective sleeve 13 corresponds to the at least ⅓ of the complete length of the catheter shaft, at the maximum to ½ of the complete length of the catheter shaft.

The catheter package 2 is shown in FIG. 1 in partly broken view. The catheter 3 is therefore not shown in its complete length. The protective sleeve 13 is preferably made of a flexible material, preferably ethylene-vinyl acetate (EVA). This leads to a very thin film with high transparency and good mechanical properties. However, the protective sleeve could also be made from other materials, for example, up to 100% polyethylene. In this case, the desired flexibility of the protective sleeve is achieved by reducing the wall thickness of the sleeve. Other stiff materials could also be used as long as the wall thickness is sufficiently thin. The maximum length of the protective sleeve 13 is at least ¾ of the length of the catheter shaft 9. For a male catheter with a length of 400 mm, the protective sleeve is in its extended position has a length of approximately 330 mm. When the catheter 3 with the protective sleeve 13 is arranged in the catheter package 2, the protective sleeve 13 is in a retracted state due to the fixation of the introducer aid 16 by the weld tabs 18 of the catheter package 2.

The catheter shaft 9 is at least partly covered by a hydrophilic coating. At least the insertable length of the catheter shaft 9, that is, the length that can be inserted in the urethra of a user is covered by the hydrophilic coating. The catheter package 2 comprises two further weld seams 21 which form a separate compartment for a sachet 4 for wetting fluid. Therefore, the catheter package 2 comprises two compartments, a first compartment for the catheter 3 and the second compartment for the sachet 4 for wetting fluid. The two weld seams 21 form a channel 22 which allows a permanent fluid communication between the first compartment for the catheter 3 and a second compartment for the sachet 4 for wetting fluid. The catheter 3 is arranged in the catheter package 2 in such a way that the catheter tip 11 is arranged near the channel 22 which is formed by the two weld seams 21 of the catheter package 2. The sachet 4 for the wetting fluid is also made of a material which is impermeable to water and water vapour. The wetting fluid is preferably water or a saline solution.

The protective sleeve can also be made of a stiffer material which is prefolded into a concertina pleated configuration and which is unfolded when pulling the catheter out of the catheter package.

FIG. 2 shows a perspective view of the introducer aid 16 of the ready to use catheter assembly 1. The introducer aid 16 has the form of a hollow cylinder. However, the proximal end 23 of the introducer aid 16 has a diameter D which is lightly larger than the diameter d of the distal end 24 of the introducer aid 16. Preferably, the diameter D of the proximal end 23 of the introducer aid 16 is approximately 1.1 times the diameter d of the distal end 24 of the introducer aid 16. Therefore, a step is formed on the outer surface of the introducer aid 16 near the proximal end 23 thereof where the diameter D of the proximal end 23 is reduced to the diameter d of the distal end 24. This step functions as a stopper when the protective sleeve 13 is pulled on the introducer aid 16 and fixed thereto. As the recesses 17 lie between the step and the distal end 24, they are completely covered by the protective sleeve 13 when it is fixedly connected with the introducer aid 16. The length $L_{IA}$ of the of the introducer aid 16 is at least 20 mm, preferably at least 35 mm so that it can be easily gripped by a user when using the catheter for an intermittent catheterization. The introducer aid 16 comprises two recesses 17 on opposite sides of the introducer aid 16. The depth of the recesses 17 has its maximum approximately in the middle of the recesses 17 and has a slow inclination towards the proximal end 23 of the introducer aid 16 until they abut with the outer surface of the introducer aid 16. Towards the distal end 24 of the introducer aid 16 the recesses 17 upmount quite steeply so that a stopper is formed.

When using the catheter assembly 2, the user opens the catheter package 2 via the opening means 6, that is, by tearing the sealing flap 8 open so that the package opening 7 is opened. The length of the package opening 7 determines the defined maximum opening length of the opening means 6. As the catheter 3 is fixed in the catheter package 2 via the introducer aid 16, which is in engagement with the weld tabs 18 of the catheter package, the catheter 3 cannot slip out of the package. The whole part of the catheter shaft 9 which is exposed to the exterior via the package opening 7 is covered by the protective sleeve 13. Therefore, it can be guaranteed that the catheter shaft 9 is not brought into contact with any materials and is therefore uncontaminated and stays in the sterile state. The user then takes the catheter 3 by the funnel 10 and the part of the catheter shaft 9 covered by the protective sleeve 13 and pulls it out of the catheter package 3. As the introducer aid 16 is still in engagement with the weld tabs 18, the protective sleeve is extended until its maximum length is reached. The user then has to slightly upmount the pulling force, to pull the introducer aid 16 through the passage 19 formed by the weld tabs 18. As the recesses 17 are inclined in this direction, they form a slope and facilitate the pulling of the introducer aid 16 through the passage 19. Finally, the whole catheter 3 is released and ready for catherization.

The form of the recesses 17 is adapted to a human finger so that a user can easily grip the introducer aid 16.

In the following, a method for producing the ready to use catheter assembly is described.

In a first step, the catheter 3 with the catheter shaft 9, the funnel 10, the tip 11 and the protective sleeve 13 as well as the introducer aid 16 are assembled. Preferably, the protective sleeve 13 is fixedly connected to the introducer aid 16 along the complete length $L_{IA}$ of the introducer aid 16, for example by heat shrinking and/or an adhesive bond. The catheter 3 and the sachet 4 with wetting fluid are then placed in the catheter package 2 and the catheter package 2 is sealed at both ends with the end weld seams 5. In the same step, the weld tabs 18 which fix the introducer aid 16 in the catheter package and the weld seams 21 which form the compartment for the sachet 4 with the wetting fluid are produced.

Before inserting the catheter 3 in the package, the protective sleeve 13 is brought in the retracted state by pushing the introducer aid 16 towards the funnel 10 of the catheter 3. The whole catheter assembly 1 is then sterilized, preferably by particle and/or electromagnetic radiation. After the sterilization, the sachet 4 with the wetting fluid is burst so that the wetting fluid flows through the channel 22 towards the tip 11 of the catheter 3 and flows down along the catheter shaft 9 thereby wetting and activating the hydrophilic coating of the catheter shaft 9. The catheter assembly 2 therefore comprises an activated hydrophilic catheter which can be immediately used for intermittent catheterization without requiring any further steps.

The wetting fluid does not necessarily need to be packaged in a sachet. It is sufficient if the wetting fluid or a wetting medium with a higher viscosity is placed in the catheter package so that it is not in contact with at least the hydrophilic coating of the catheter. The wetting medium/wetting fluid must be kept separate from the hydrophilic coating during the sterilization process. After the sterilization process, the wetting fluid/wetting medium is brought into contact with the hydrophilic coating of the catheter and thereby activates the hydrophilic coating.

The catheter assembly does not necessarily need a package opening. It is also possible that the catheter package is made of two foils which are welded together along the outer circumference and that the first end of the catheter package is provided with two opening flaps at which the package can be torn open. This package also comprises weld tabs near the first end of the package which are then formed in such a way that the force needed to open these weld tabs is substantially higher than the force needed for opening the package along the circumferential weld seams which usually lies in a range of approximately 1-15N. The protective sleeve is then fixed at the catheter package at or near these weld tabs. It is sufficient if the distance between the weld tabs and the fixations of the protective sleeve to the catheter package corresponds to approximately the width of a finger of a user of the catheter. In this way, an accidental touching of the catheter shaft can be prevented and the catheter stays in the sterile condition.

List of reference numbers

1 Ready to use catheter assembly
2 Catheter package
3 Catheter
4 Sachet for the wetting fluid
5 End weld seam
6 Opening means
7 Package opening
8 Sealing flap
9 Catheter shaft
10 Funnel
11 Catheter tip
12 Catheter eye
13 Protective sleeve
14 Distal end of protective sleeve
15 Proximal end of protective sleeve
16 Introducer aid
17 Recess
18 Weld tab
19 Passage
20 First end of catheter package
21 Weld seam
22 Channel
23 Proximal end of introducer aid 24 Distal end of introducer aid
B Width of catheter package
L Length of catheter package
D Diameter of the proximal end of introducer aid
d Diameter of the distal end of introducer aid
$L_{IA}$ Length of introducer aid

The invention claimed is:

1. A ready to use catheter assembly comprising:
a catheter package with an opening means;
a catheter with a catheter shaft which is arranged in the catheter package so that a distal end of the catheter lies in the region of the opening means; and
a protective sleeve which at least partly covers the catheter shaft, wherein a first end of the protective sleeve is fixed to the distal end of the catheter,
wherein
the opening means has a defined maximum opening length, and a second end of the protective sleeve is releasably connected with the catheter package near the maximum opening length of the opening means and the protective sleeve is in a retracted state.

2. The ready to use catheter assembly according to claim 1, wherein a length of the protective sleeve in an extended state is at least ⅔ of a length of the catheter shaft.

3. The ready to use catheter assembly according to claim 1, further comprising an introducer aid in the form of a hollow cylinder arranged on the catheter shaft, the introducer aid is fixedly connected with the second end of protective sleeve and releasably connected with the catheter package near the maximum opening length of the opening means.

4. The ready to use catheter assembly according to claim 3, wherein the catheter package comprises at least one protrusion which is in releasable engagement with the introducer aid.

5. The ready to use catheter assembly according to claim 4, wherein the at least one protrusion is a weld tab.

6. The ready to use catheter assembly according to claim 4, wherein the introducer aid comprises at least one recess which is in releasable engagement with the at least one protrusion of the catheter package.

7. The ready to use catheter assembly according to claim 6, wherein the at least one recess of the introducer aid has a stopper at the end facing the distal end of the catheter and an inclination at the end facing the proximal end of the catheter.

8. The ready to use catheter assembly according to claim 6, wherein the at least one recess of the introducer aid completely penetrates the wall of the introducer aid.

9. The ready to use catheter assembly according to claim 1, wherein the protective sleeve is made of a flexible material.

10. The ready to use catheter assembly according to claim 3, wherein the protective sleeve is fixed to the introducer aid along a complete length of the introducer aid.

11. The ready to use catheter assembly according to claim 1, wherein a length of the catheter shaft that is covered by the protective sleeve in the retracted state corresponds to at least ¼ of a complete length of the catheter shaft.

12. The ready to use catheter assembly according to claim 3, wherein a diameter of a proximal end of the introducer aid corresponds to at least 0.75 times a diameter of a passage in the catheter package created by the at least one protrusion of the catheter package.

13. The ready to use catheter assembly according to claim 1, further comprising a sachet containing a wetting fluid which is arranged in the catheter package near the catheter tip so that the wetting fluid is not in contact with the catheter.

14. The ready to use catheter assembly according to claim 13, wherein the catheter package comprises a first compartment for the sachet for wetting fluid and a second compartment for the catheter and that the two compartments are in permanent fluid communication with each other.

15. The ready to use catheter assembly according to claim 1, wherein the catheter shaft is at least partly covered with an activated hydrophilic coating.

16. A method of making a ready to use catheter assembly according to claim 1, comprising the following steps:
placing the hydrophilic coated catheter with the introducer aid and the protective sleeve in the catheter package so that the protective sleeve is in a retracted position in the region of the opening means with the defined maximum opening length,
placing the wetting fluid into the catheter package so that it is separate from the catheter,
sterilizing the complete catheter assembly, and then
activating the hydrophilic coating of the catheter by bringing the wetting fluid into contact with the hydrophilic coating of the catheter.

* * * * *